(12) United States Patent
Zhou

(10) Patent No.: US 8,850,606 B2
(45) Date of Patent: Sep. 30, 2014

(54) COMPUTER READABLE MEDIUM STORING PROGRAM, INFORMATION PROCESSING APPARATUS, AND INFORMATION PROCESSING METHOD FOR DOCUMENT SECURITY

(75) Inventor: Bin Zhou, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 597 days.

(21) Appl. No.: 12/697,319

(22) Filed: Feb. 1, 2010

(65) Prior Publication Data
US 2011/0016535 A1 Jan. 20, 2011

(30) Foreign Application Priority Data
Jul. 15, 2009 (JP) ................................ 2009-166425

(51) Int. Cl.
G06F 7/04 (2006.01)
G06F 21/64 (2013.01)
G06F 19/00 (2011.01)

(52) U.S. Cl.
CPC .............. G06F 21/64 (2013.01); *G06F 19/322* (2013.01)
USPC ........................................... 726/30; 707/608

(58) Field of Classification Search
CPC ......... G06F 21/16; G06F 21/60; G06F 21/64; G06F 19/32–19/323; Y10S 283/90
USPC ................ 726/26–27, 30; 713/182, 185–186; 707/608, 687, 700, 737–738, 758
See application file for complete search history.

(56) References Cited

U.S. PATENT DOCUMENTS

| | | | |
|---|---|---|---|
| 6,021,202 A * | 2/2000 | Anderson et al. | 705/54 |
| 6,959,384 B1 * | 10/2005 | Serret-Avila | 713/176 |
| 7,181,017 B1 * | 2/2007 | Nagel et al. | 380/282 |
| 7,436,975 B2 * | 10/2008 | Shibata | 382/100 |

(Continued)

FOREIGN PATENT DOCUMENTS

| JP | 2001-331104 A | 11/2001 |
|---|---|---|
| JP | 2002092155 A | 3/2002 |

(Continued)

OTHER PUBLICATIONS

Dworkin, Morris, "Recommendation for Block Cipher Modes of Operation: Galois/Counter Mode (GCM) and GMAC" [Online], National Institute of Standards and Technology, Nov. 2007 [Retrieved on: Jun. 2, 2012], [Retrieved from: http://csrc.nist.gov/publications/nistpubs/800-38D/SP-800-38D.pdf].*

(Continued)

*Primary Examiner* — Saleh Najjar
*Assistant Examiner* — Eric W Shepperd
(74) *Attorney, Agent, or Firm* — Sughrue Mion, PLLC

(57) ABSTRACT

A computer readable medium storing a program causing a computer to execute a process for information processing, the process includes: receiving a first characteristic value calculated on the basis of first document information for use in detecting whether the first document information is tampered with or not; receiving a second characteristic value calculated on the basis of second document information for use in detecting whether the second document information is tampered with or not; and calculating a third characteristic value for use in detecting whether third document information is tampered with or not on the basis of the first characteristic value, the second characteristic value and the third document information related to integration of the first document information and the second document information.

8 Claims, 11 Drawing Sheets

(56) References Cited

U.S. PATENT DOCUMENTS

| | | | |
|---|---|---|---|
| 7,620,976 B2* | 11/2009 | Low et al. | 726/4 |
| 7,668,820 B2* | 2/2010 | Zuleba | 707/765 |
| 7,725,330 B2* | 5/2010 | Rao et al. | 705/3 |
| 7,730,490 B2* | 6/2010 | Ito | 718/106 |
| 7,765,474 B2* | 7/2010 | Terao et al. | 715/255 |
| 7,802,183 B1* | 9/2010 | Essin | 715/255 |
| 7,930,548 B2* | 4/2011 | Wakao | 713/176 |
| 7,958,367 B2* | 6/2011 | Uesugi et al. | 713/178 |
| 7,973,959 B2* | 7/2011 | Chihara | 358/1.15 |
| 8,005,850 B2* | 8/2011 | Walther et al. | 707/758 |
| 2006/0034453 A1* | 2/2006 | Liu | 380/28 |
| 2007/0271316 A1* | 11/2007 | Hollebeek | 707/204 |
| 2007/0299697 A1* | 12/2007 | Friedlander et al. | 705/3 |
| 2008/0104104 A1* | 5/2008 | Nolan et al. | 707/102 |
| 2009/0249220 A1* | 10/2009 | Golle et al. | 715/751 |
| 2010/0161353 A1* | 6/2010 | Mayaud | 705/3 |
| 2010/0179834 A1* | 7/2010 | Wager | 705/3 |
| 2011/0010195 A1* | 1/2011 | Cohn | 705/3 |
| 2011/0119307 A1* | 5/2011 | Unger et al. | 707/783 |

FOREIGN PATENT DOCUMENTS

| | | |
|---|---|---|
| JP | 2003303185 A | 10/2003 |
| JP | 2004-40830 A | 2/2004 |
| JP | 2005084709 A | 3/2005 |
| JP | 2006067094 A | 3/2006 |
| JP | 2007148544 A | 6/2007 |

OTHER PUBLICATIONS

Lindholm, Tancred "A Three-way Merge for XML Documents" [Online], Oct. 30, 2004 [Retrieved on: Dec. 10, 2012]; ACM [www.acm.org]; DocEng 2004 [Retrieved from: http://delivery.acm.org/10.1145/1040000/1030399/p1-lindholm.pdf].*

Japanese Office Action dated Aug. 6, 2013, issued in corresponding Japanese Patent Application No. 2009-166425.

* cited by examiner

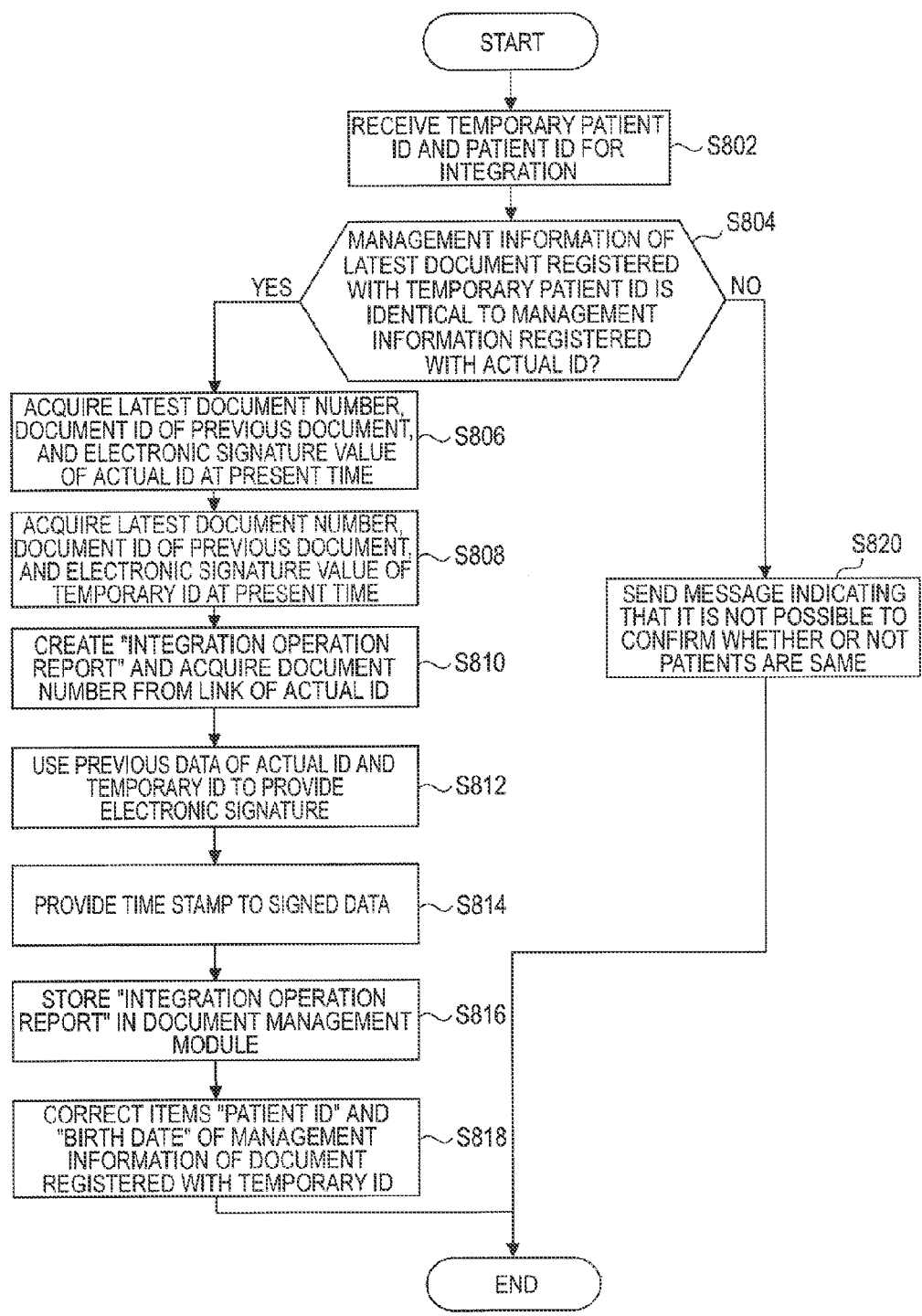

FIG.9

| 510 | 520 | 530 | 540 | 550 | 561 | 562 | 563 | 564 | 565 | 566 | 567 | 568 | 569 |
|---|---|---|---|---|---|---|---|---|---|---|---|---|---|
| | DOCUMENT ID | DOCUMENT NAME | ELECTRONIC SIGNATURE VALUE | TIME STAMP VALUE | PATIENT ID | ID OF PREVIOUS DOCUMENT | DOCUMENT NUMBER | NAME | BIRTH DATE | SEX | HEIGHT | BLOOD TYPE (ABO) | BLOOD TYPE (RH) |
| DATA | aaaa.bbbb | AAA | XXX | XXX | 11111 | | 1 | AI | 1990/11/10 | M | 179.6 | A | - |
| DATA | aaaa.cccc | III | XXX | XXX | TEMPORARY 123 | | 1 | | 1988/1/1 | M | 179.4 | A | - |
| DATA | aaaa.1111 | SASASA | XXX | XXX | TEMPORARY 123 | aaaa.cccc | 2 | | 1988/1/1 | M | 179.4 | A | - |
| DATA | aaaa.ddddd | UUU | XXX | XXX | 11111 | aaaa.bbbb | 2 | AI | 1990/11/10 | M | 179.5 | A | - |
| DATA | aaaa.eeee | EEE | XXX | XXX | 11111 | aaaa.ddddd | 3 | AI | 1990/11/10 | M | 179.6 | A | - |

500 — MANAGEMENT INFORMATION

FIG.12

| | DOCUMENT | DOCUMENT ID | DOCUMENT NAME | ELECTRONIC SIGNATURE VALUE | TIME STAMP VALUE | PATIENT ID | ID OF PREVIOUS DOCUMENT | DOCUMENT NUMBER | NAME | BIRTH DATE | SEX | HEIGHT | BLOOD TYPE (ABO) | BLOOD TYPE (RH) |
|---|---|---|---|---|---|---|---|---|---|---|---|---|---|---|
| INTEGRATION CHECK | DATA | aaaa.1111 | SASASA | XXX | XXX | TEMPORARY 123 | aaaa.cccc | 2 | | 1988/1/1 | M | 179.4 | A | - |
| | DATA | aaaa.eeee | EEE | XXX | XXX | 11111 | aaaa.ddddd | 3 | AI | 1990/11/10 | M | 179.6 | A | - |
| INTEGRATION DIFFERENCE CALCULATION RESULT | N/A | N/A | N/A | N/A | N/A | N/A | N/A | N/A | N/A | TWO YEARS | IDENTICAL | 0.2 | IDENTICAL | IDENTICAL |
| ALLOWABLE ERROR RANGE | N/A | N/A | N/A | N/A | N/A | N/A | N/A | N/A | N/A | TEN YEARS | IDENTICAL | 10 | IDENTICAL | IDENTICAL |
| DETERMINATION RESULT | | | | | | | | | | PERMITTED | PERMITTED | PERMITTED | PERMITTED | PERMITTED |

COMPUTER READABLE MEDIUM STORING PROGRAM, INFORMATION PROCESSING APPARATUS, AND INFORMATION PROCESSING METHOD FOR DOCUMENT SECURITY

CROSS-REFERENCE TO RELATED APPLICATIONS

This application is based on and claims priority under 35 USC 119 from Japanese Patent Application No. 2009-166425 filed on Jul. 15, 2009.

BACKGROUND

1. Technical Field

The invention relates to a computer readable medium storing program, an information processing apparatus and an information processing method.

2. Related Art

In order to ensure security of document information, a technique for falsification detection is demanded.

SUMMARY

According to an aspect of the present invention, there is provided a computer readable medium storing a program causing a computer to execute a process for information processing, the process including: receiving a first characteristic value calculated on the basis of first document information for use in detecting whether the first document information is tampered with or not; receiving a second characteristic value calculated on the basis of second document information for use in detecting whether the second document information is tampered with or not; and calculating a third characteristic value for use in detecting whether third document information is tampered with or not on the basis of the first characteristic value, the second characteristic value and the third document information related to integration of the first document information and the second document information.

BRIEF DESCRIPTION OF THE DRAWINGS

An exemplary embodiment of the invention will be described in detail based on the following figures, wherein:

FIG. 8 is a flowchart showing an example of processing for integrating a first document group and a second document group according to this exemplary embodiment;

FIG. 9 is an explanatory view showing an example of the data structure of a document data table before integration processing according to this exemplary embodiment;

FIG. 12 is an explanatory view showing an example of the data structure of a same person check table.

DETAILED DESCRIPTION

Hereinafter, an exemplary embodiment for realizing the invention will be described with reference to the drawings.

Figure 1:
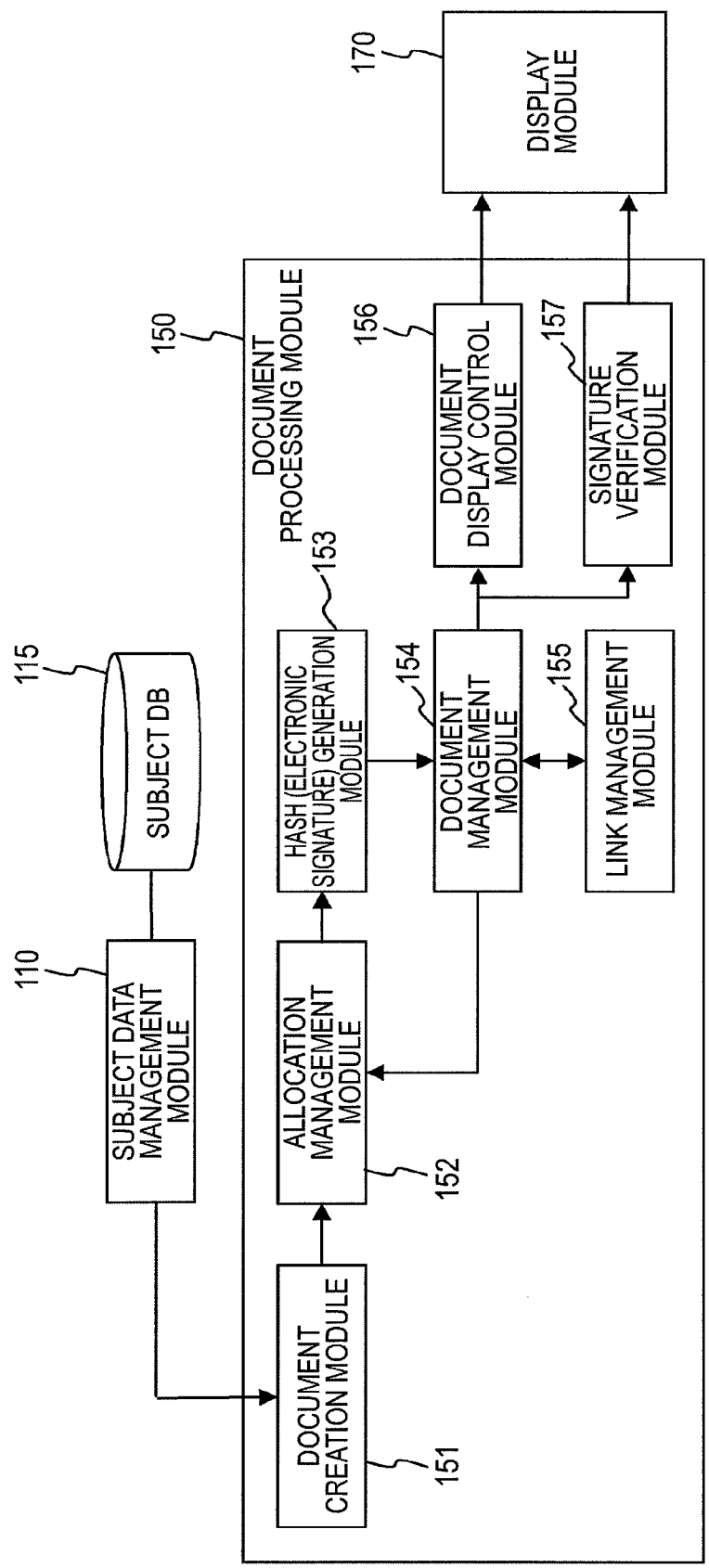
FIG. 1 is a diagram showing a conceptual module configuration for a configuration example of this exemplary embodiment.

FIG. 1 is a diagram showing a conceptual module configuration for a configuration example of this exemplary embodiment.

The module generally means software that is logically separable (computer program), and hardware parts. Accordingly, the module in the exemplary embodiment means not only a module in a computer program but also a module in a hardware configuration. Therefore, the exemplary embodiment describes a computer program, a system and also a method. Though "store", "let store", and a word equivalent to these words are used for convenience of description, these words mean, in the case where the exemplary embodiment is the computer program, "to let a storage device store" or "to perform such control as to let a storage device store". A module corresponds to a function in nearly one-to-one relation. Regarding mounting, one module may be configured by one program, plural modules may be configured by one program, and to the contrary, one module may be configured by plural programs. The plural modules may be executed by one computer, or one module may be executed by plural computers arranged in a distribution environment or in parallel environment. Another module may be included in one module. The term "connection" includes physical connection and also logical connection (data delivery and reception, instruction, and reference relation between data).

A system or a device is configured by plural computers, hardware, a device, or the like which are connected by communication means, such as a network (including one-to-one communication connection), or can also be implemented by one computer, hardware, a device, or the like. The terms "device" and "system" are synonymous. The term "set in advance" refers to being determined before target processing, and includes being determined in accordance with the situation or state at that time or in accordance with the previous situation or state if target processing has not yet been performed, regardless of before and after the start of processing of this exemplary embodiment. Although the term "management" is used, this means control, management, or storage of data for control or management in accordance with the context, or function or operation.

The term "document information" refers to text data, as occasion demands, electronic data, such as an image, a motion image, or sound, or a combination thereof. The document information can be stored, edited, or searched, and can be transferred between systems or users as the individual unit. The term "document information" also includes the materials similar thereto. Hereinafter, document information is also referred to as document. Though content is not limited, the description will be made for a document regarding a patient in a medical field (specifically, medical record, X-ray picture, test result, and the like). The term "document group" refers to plural documents generated for the same target, and for example, includes medical records generated in time series for the same patient or the like.

A characteristic value of a document is calculated on the basis of the document, and can be used to detect whether the document is tampered with or not. Herein, the description will be made for a hash value.

An information processing program of this exemplary embodiment manages document information for detection of falsification of a document. As shown in FIG. 1, the information processing program has a subject data management module 110, a subject DB 115, a document processing module 150, and a display module 170.

The subject data management module 110 is connected to the subject DB 115 and a document creation module 151. For example, the subject data management module 110 generates or receives, for example, a patient ID (IDentifier) for uniquely identifying a patient, information regarding the patient, and the like, and stores and manages the patient ID and the information regarding the patient in the subject DB 115. The subject data management module 110 transfers the information regarding the patient and the like in response to a request from the document creation module 151 of the document processing module 150.

The subject DB 115 is accessed from the subject data management module 110. The subject DB 115 stores the information regarding the patient and the like generated by the subject data management module 110.

The document processing module 150 has a document creation module 151, an allocation management module 152, a hash (electronic signature) generation module 153, a document management module 154, a link management module 155, a document display control module 156, and a signature verification module 157.

The document creation module 151 is connected to the subject data management module 110 and the allocation management module 152. The document creation module 151 opens an existing document or newly creates a document in accordance with an edit instruction from a user. When generating the document, the document creation module 151 obtains the information regarding the patient and the like from the subject data management module 110. A completed document is transferred to the allocation management module 152.

The allocation management module 152 is connected to the document creation module 151, the hash (electronic signature) generation module 153, and the document management module 154. The allocation management module 152 generates an incremental number of a document (hereinafter, also referred to as document number) for each patient ID. The allocation management module 152 also manages registered IDs of the document management module 154. A document assigned with a document number is transferred to the hash (electronic signature) generation module 153.

The hash (electronic signature) generation module 153 is connected to the allocation management module 152 and the document management module 154. The hash (electronic signature) generation module 153 provides an electronic signature including a hash value (or electronic signature value) of a document previously registered to a current document. A document with an electronic signature is transferred to the document management module 154.

The document management module 154 is connected to the allocation management module 152, the hash (electronic signature) generation module 153, the link management module 155, the document display control module 156, and the signature verification module 157. The document management module 154 has a function to certify that the document is original, and manages a document in a storage device. The document management module 154 manages actual data of documents, electronic signature data, management information of documents, and the like, and provides a document ID to each document so as to uniquely identify the document. The document management module 154 receives a document transferred from the hash (electronic signature) generation module 153 or the link management module 155, and transfers the document to the document display control module 156 on the basis of a document display instruction from the user, or transfers a document to be verified to the signature verification module 157.

The link management module 155 is connected to the document management module 154. The link management module 155 integrates a link of a document generated with a temporary patient ID with a link of an actual patient ID of the same patient. At this time, the link management module 155 performs a check by management data. Further, the link management module 155 receives an integration instruction from the user at the time of integration, and generates a document for link.

The link management module 155 receives a hash value A of a document A for an actual patient ID, receives a hash value B of a document B for a temporary patient ID, and calculates a hash value C of the document for link on the basis of the received hash value A and hash value B and the document for link related to integration of the document A and the document B.

When receiving an instruction to integrate the document A and the document B, the link management module 155 may generate a document for link indicating integration of the document A and the document B.

The link management module 155 may generate a document for link that includes user information (user ID, user name, and the like) for identifying a user involved in integration of the document A and the document B.

The link management module 155 may generate a document for link so as to include an indication that a patient of the temporary patient ID for the document B is a patient of the actual patient ID for the document A.

The link management module 155 may generate a document for link including an execution request regarding integration of the document A and the document B and an execution confirmation that the integration is executed.

The link management module 155 may determine whether the patient of the actual patient ID for the document A is the same as the patient of the temporary patient ID for the document B or not on the basis of a determination criterion set in advance, and when it is determined to be the same person, may perform processing for integrating the document A and the document B. When it is determined to be not the same person, the user may be requested to determine whether the patient of the actual patient ID is the same as the patient of the temporary patient ID or not, and when the user determines to be the same person (the user operation indicates the same person), a document for link including an execution request and an execution confirmation may be generated, and the processing for integrating the document A and the document B may be performed.

The document display control module 156 is connected to the document management module 154 and the display module 170. The document display control module 156 displays a document received from the document management module 154 on the display module 170.

The signature verification module 157 is connected to the document management module 154 and the display module 170. The signature verification module 157 verifies the electronic signature of each document managed by the document management module 154 and a link of the electronic signature, and displays the result on the display module 170.

The display module 170 is connected to the document display control module 156 and the signature verification module 157 of the document processing module 150. The display module 170 displays a document, a signature verification result, and the like on a display or the like.

The preconditions in this exemplary embodiment will be described.

First, it is necessary to use a method of specifying a patient by a patient ID. In general, a document is created for every patient with a patient ID identified. However, when the identity of a patient cannot be specified, for example, at the time of emergency, a temporary patient ID is provided. In this case, the patient with a temporary patient ID may be identified later as a patient with a regular patient ID.

Next, the document management module 154 needs to manage a set of the content of a document and management information.

Figure 2:
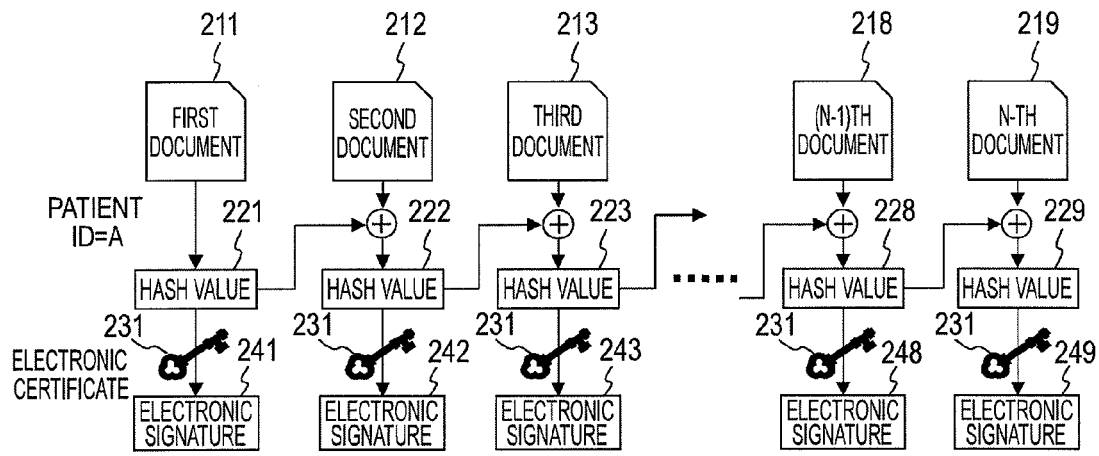
FIG. 2 is an explanatory view showing an example of processing for generating a document group according to this exemplary embodiment.
Figure 3:
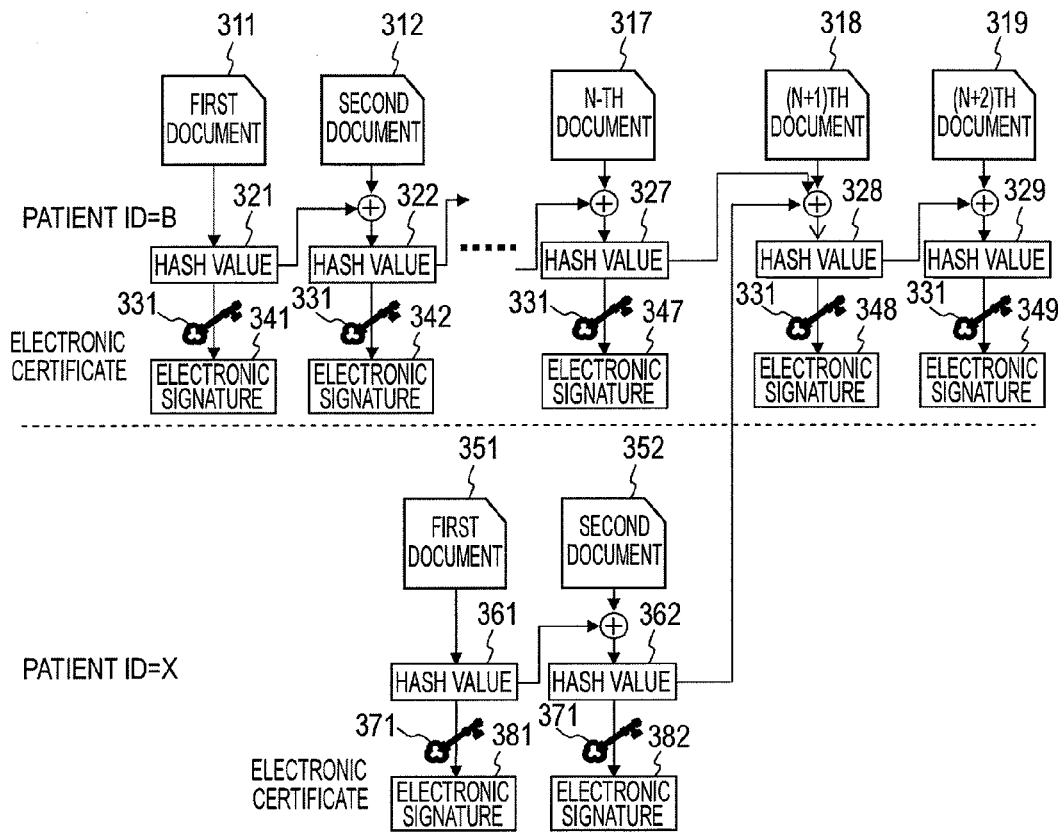
FIG. 3 is an explanatory view showing an example of processing for integrating a first document group and a second document group according to this exemplary embodiment.

Hereinafter, various kinds of processing in this exemplary embodiment, (A) document registration processing for a new patient, (B) document registration processing for an existing patient who has already been registered, (C) document registration processing for a patient with an unknown patient ID, (D) integration processing of a temporary patient ID and a patient ID of a new patient, (E) integration processing a temporary patient ID and an existing patient ID of an existing patient, and (F) verification processing of a document link, will be described with reference to FIGS. 2 and 3. FIG. 2 is an explanatory view showing an example of processing for generating a document group according to this exemplary embodiment. FIG. 3 is an explanatory view showing an example of processing for integrating a first document group and a second document group according to this exemplary embodiment.

The documents are generated in time series for each patient. Therefore, a previous document refers to a document created before a target document created at present and temporally nearest to the target document.

(A) Registration 1: Document Registration Processing for New Patient

[A1] A regular patient ID is issued from the subject data management module 110 of the hospital.

[A2] After a document is created by the document creation module 151, the patient ID and the document are transmitted to the allocation management module 152, and registration processing starts.

[A3] Since there is no previous document for the relevant patient ID, the allocation management module 152 sets a latest document number to 1 and sets the latest document number as the document number of the registered document at present.

[A4] The hash (electronic signature) generation module 153 provides an electronic signature of a signer to the entity of the document to be registered. Since there is no document that has been registered previously, only the entity of the document is used for hash generation. As shown in FIG. 2, a hash value 221 is generated from a first document 211, and performs an electronic signature 241 by using an electronic certificate 231.

[A5] Management information includes the document, the electronic signature value, the document ID of the previous document (there is no previous document because of an initial document), and personal information of the patient is managed by the document management module 154.

(B) Registration 2: Document Registration Processing for Existing Patient Who has Already been Registered

[B1] Since there is a patient ID, issuance of a patient ID is not required. After a document is created by the document creation module 151, the patient ID and the document are transmitted to the allocation management module 152, and registration processing starts.

[B2] The allocation management module 152 increments the latest document number of the relevant patient ID by one, and sets the updated latest document number as the document number of the document to be registered.

[B3] The hash (electronic signature) generation module 153 provides the electronic signature of the signer to data including the entity of the document to be registered and a hash value (or electronic signature value) of a document previously registered. As shown in FIG. 2, this is applied to a second document 212 and later. That is, in the case of a second document 212, a hash value 222 is generated from the second document 212 (the entity of the second document) and a hash value 221, and an electronic signature 242 is generated by using an electronic certificate 231. The hash value 222 is used to register a next third document 213. Hash value 223 may then be derived for the third document 213, and so forth to N documents, as shown at documents 218, 219, and hash values 228 and 229. Electronic signatures 243, 248, 249 may also be similarly generated based on electronic certificate 231.

[B4] Management information including the document, the electronic signature value, the document ID of the previous document, and personal information of the patient is managed by the document management module 154.

(C) Registration 3: Document Registration Processing for Patient with Unknown Patient ID

[C1] A temporary patient ID is issued from the subject data management module 110 of the hospital.

[C2] After a document is created by the document creation module 151, the temporary patient ID and the document are transmitted to the allocation management module 152, and registration processing starts.

[C3] When there is no previous document for the relevant temporary patient ID, the allocation management module 152 sets the latest document number to one, and sets the latest document number as the document number of the registered document at present. When subsequent documents are registered, the latest document number is incremented by one, and the updated document number is set as the document number of a document to be registered.

[C4] When there is no previous document, the hash (electronic signature) generation module 153 provides the electronic signature of the signer to the entity of the document to be registered. Since there is no document that has been registered previously, only the entity of the document is used for hash generation. As shown in FIG. 3, a hash value 361 is generated from a first document 351, and an electronic signature 381 is performed by using an electronic certificate 371. When there is a previous document, the electronic signature of the signer is provided to the entity of the document to be registered and data of the hash value (or electronic signature value) of a document that has been registered previously.

[C5] Management information including the document, the electronic signature value, the document ID of the previous document (in the case of an initial document, there is no document ID of a previous document), and personal information of the patient is managed by the document management module 154.

(D) Link Integration 1: Integration Processing of Temporary Patient ID and Patient ID of New Patient

[D1] When a patient who uses a temporary patient ID is identified, a regular patient ID is issued from the subject data management module 110 of the hospital, and link integration processing is performed.

[D2] At the time of integration, since there is no previous document for the new patient ID, a check for the same person is omitted.

[D3] When receiving an instruction from the user, the link management module 155 creates a document (for example, integration report) in which an integration indication is described, and registers the document. Since there is no previous document for the relevant patient ID, the allocation management module 152 sets the latest document number to one, and sets the latest document number as the document number of the integration report.

[D4] The electronic signature of the signer is provided to the entity of the document to be registered (integration report) and data of a hash value (or electronic signature) of a previous document that has been registered previously with the temporary patient ID.

[D5] Management information including a document, the electronic signature value, the document ID of the previous document, and personal information of the patient is managed by the document management module 154.

[D6] Data of "patient ID" and "birth date" in the management information of the document created with the temporary patient ID to be integrated is updated so as to be identical to latest data of the actual patient ID (for example, data acquired from another system in the hospital).

(E) Link Integration 2: Integration Processing of Temporary Patient ID and Existing Patient ID of Existing Patient

[E1] When a patient who uses a temporary patient ID is identified, since the actual patient ID of the patient is used, issuance of a patient ID is not required.

[E2] At the time of integration, the link management module 155 uses management information of a document and checks for the same person so as to prevent incorrect integration due to intention or misallocation of a patient ID. It is assumed that management information of the existing information cannot be corrected by a registered person and an instructor for integration. When the check result is inconsistent, integration processing may be interrupted, and thereafter, the integration processing may be performed depending on the determination of the user.

The check for the same person is performed as follows.

(1) Check by Physical Information

A previous document of an actual patient ID of a patient and management information of a previous document of a temporary patient ID are acquired, and a check is performed regarding whether the sex, height, blood type, age, and the like are identical. A tolerance is provided for height and age.

(2) Check by Name and Birth Date

Before integration, there are many cases where the patient name in the management information of the document of the temporary patient ID is blank. In this case, first, the user requests an institution having authority to correct management information to update the patient name and pronunciation and the birth date in the document of the temporary patient ID, and a check is performed regarding the name and pronunciation and the birth date. In this case, all of the name and pronunciation and the birth date needs to be identical.

(3) Check by Biometric Authentication

When biometric authentication data, such as a fingerprint, a vein pattern, or the like, can be extracted, biometric authentication data is used for the check for the same person.

[E3] An instruction from the user is received, the link management module 155 creates a document (for example, integration report), in which an integration indication is described, and registers the document. The allocation management module 152 increments the latest document number of the relevant patient ID by one, and sets the updated latest document number as the document number of the integration report. This document corresponds to an (N+1)th document 318 shown in FIG. 3. That is, a hash value 328 is generated from the (N+1)th document 318 (the entity of the (N+1)th document), a hash value 327, and a hash value 362, and an electronic signature 348 is generated by using an electronic certificate 331. The hash value 328 is used to register a next (N+2)th document 319. FIG. 3 illustrates the registration in view of a series of documents 311, 312, 317, 318, 319, 351, 352, with corresponding hash values 321, 322, 327, 328, 329, 361, 362, and electronic signatures 341, 342, 347, 348, 349, 381, 382.

[E4] The electronic signature of the signer is provided to data including the entity of the document to be registered (integration report) and data of the hash value (or electronic signature) of a previous document of the actual patient ID and the hash value (or electronic signature) of a previous document of the temporary ID.

[E5] Management information including the document, the electronic signature value, the document ID of the previous document of the actual patient ID, the document ID of the previous document of the temporary patient ID, and personal information of the patient is managed by the document management module 154.

[E6] Data of "patient ID" and "birth date" in the management information of the document created with the temporary patient ID to be integrated is updated so as to be identical to latest data of the actual patient ID (for example, data acquired from another system in the hospital).

(F) Verification Processing of Document Link (a Document Group Having Plural Documents for Every Patient in a Time-Dependent Manner and being Subjected to the Above-Described Registration Processing (Including Integration Processing))

[F1] The electronic signature value of the document A registered lastly in the document link is decoded with a public key, and if the electronic signature value is identical to the hash value of data to be signed, it is determined that the document A is not tampered with.

[F2] If the hash value of the document B (previous document) in data to be signed of the document A is identical to the value obtained from the hash value of the document B (previous document) and the entity of the document B by hash calculation, it is found that there is no extraction between the document B and the document A.

[F3] Thereafter, the above-described procedure is repeatedly executed, so it can be found that there is no falsification of a document and no leakage in the document link. When the electronic signature is used in the document link, instead of the document hash value, if the electronic certificate is decoded by the public key, verification of the hash value can be executed in the same manner.

Next, processing for creating a document for link (in the above-described example, integration report) when two documents are integrated will be described.

At the time of integration, if the user instructs the document processing module 150 "to manage a document list created for an urgent patient X as the documents of the patient B", the link management module 155 generates a document for link. The document for link is as follows.

(1) The link management module 155 generates a document for link so as to include identification information indicating the user who instructs integration.

Basically, since an electronic signature is provided to a document, when each user possesses an electronic certificate and signs, the electronic signature of the signer can be used to identify the user who instructs integration. However, actually, there are many cases where the signer becomes a person who is responsible for an organization or a person who is responsible for document management, not an actual user. Even when the signer is not identical to the user, if information including the ID of the user who instructs integration is recorded in the body of the document for link or management attribute, a person who executes integration can be traced. For example, when a mistake in integration, such as a difference between patient IDs to be integrated or the like, is found, the user who instructs integration can be identified by the document for link. To suppress incorrect integration, when the integration instruction is received, the indication may be displayed.

To create such a document for link, the integration instruction is received after the user ID of the user who instructs integration is received. For example, the user ID may be read from an IC card, which stores the user ID.

(2) The link management module 155 generates a document for link so as to include an indication that the urgent patient is the patient to be integrated (for example, a message indicating that "the patient X is the patient B").

After integration, management information of the document registered with the temporary patient ID is corrected to management information for the actual patient ID. Thus, if the actual patient ID is used, documents including a document at the time of emergency can be searched. However, a physician for emergency service who executes emergency treatment knows only the temporary patient ID. The patient recovers later and is identified after department transfer, and document link integration is performed. When the physician for emergency service wants to confirm the document of the patient, since the physician does not know the actual patient ID, name, birth date, and the like of the patient, it is difficult for the physician to search the document of the patient. In such a case, the actual patient ID and the temporary patient ID of the patient are described in the document for link, and sequential confirmation (or full-text search) is performed on the document for link, thereby finding the actual patient ID from the temporary patient ID.

(3) The document for link is divided into two (or more) documents of an execution request and an execution confirmation, such that two or more users should be involved.

The user instructs the document processing module 150 to execute integration, and the execution request is created and stored. Thereafter, the request is confirmed by another user (a higher-ranking person in an organization, a system administrator, or the like), and the execution confirmation is generated. Then, integration is executed such that the document for link includes the execution request and the execution confirmation.

(4) The method described in (3) that divides the document for link into two or more documents is not used during a normal operation. This method may be applied only to a case where the user checks and determines to be the same person, and integration is executed when the check for the same person using the management information at the time of integration has failed.

Next, description will be made with reference to a detailed example.

For example, a patient that is transported urgently receives treatment in a state where the patient ID is unknown, and plural documents are created. Afterwards, the patient ID of the patient is known, and integration is executed to link the documents created at the time of emergency with the existing documents of the actual patient ID. This processing will be described below. The flow of the processing includes the following operations.

(1) A document is created in a state where there is no previous document, allocation is performed, and the document is registered.

(2) A document is created in a state where there is a previous document, allocation is performed, and the document is registered.

(3) The document link of the temporary patient ID is integrated to the document link of the actual patient ID.

(4) Completeness of the documents is verified.

(1) A document is created in a state where there is no previous document, allocation is performed, and the document is registered.

A patient who initially receives treatment undergoes registration at a reception desk, and a patient ID is issued. When it is unknown whether the patient has a patient ID or not, a temporary patient ID is provided. In any case, with regard to a patient who is given a patient ID initially, there is no previous document.

Figure 6:
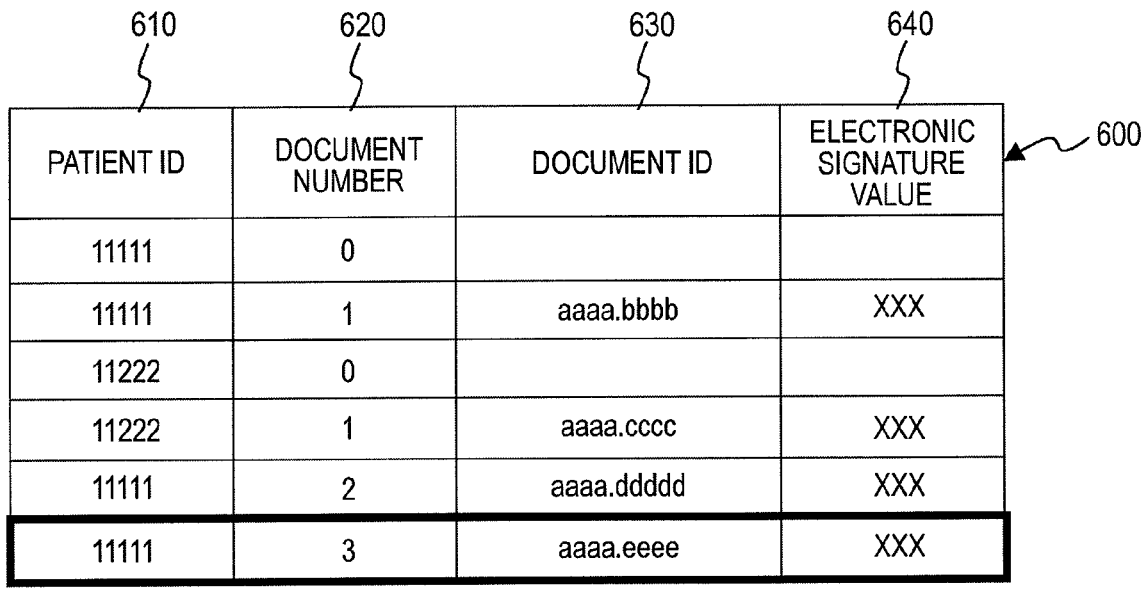
FIG. 6 is an explanatory view showing an example of the data structure of a document number table.

Allocation data by the allocation management module 152 is recorded as shown in FIG. 6. FIG. 6 is an explanatory view showing an example of the data structure of a document number table 600. The document number table 600 has a patient ID field 610, a document number field 620, a document ID field 630, and an electronic signature value field 640. The document number table 600 is a subset of the document data table 500.

The patient ID filed 610 stores the patient ID.

The document number field 620 stores the document number of a document for the patient with the patient ID (the document number generated by the allocation management module 152).

The document ID field 630 stores the document ID for uniquely identifying the document.

The electronic signature value field 640 stores the electronic signature value generated from the document.

Figure 4:
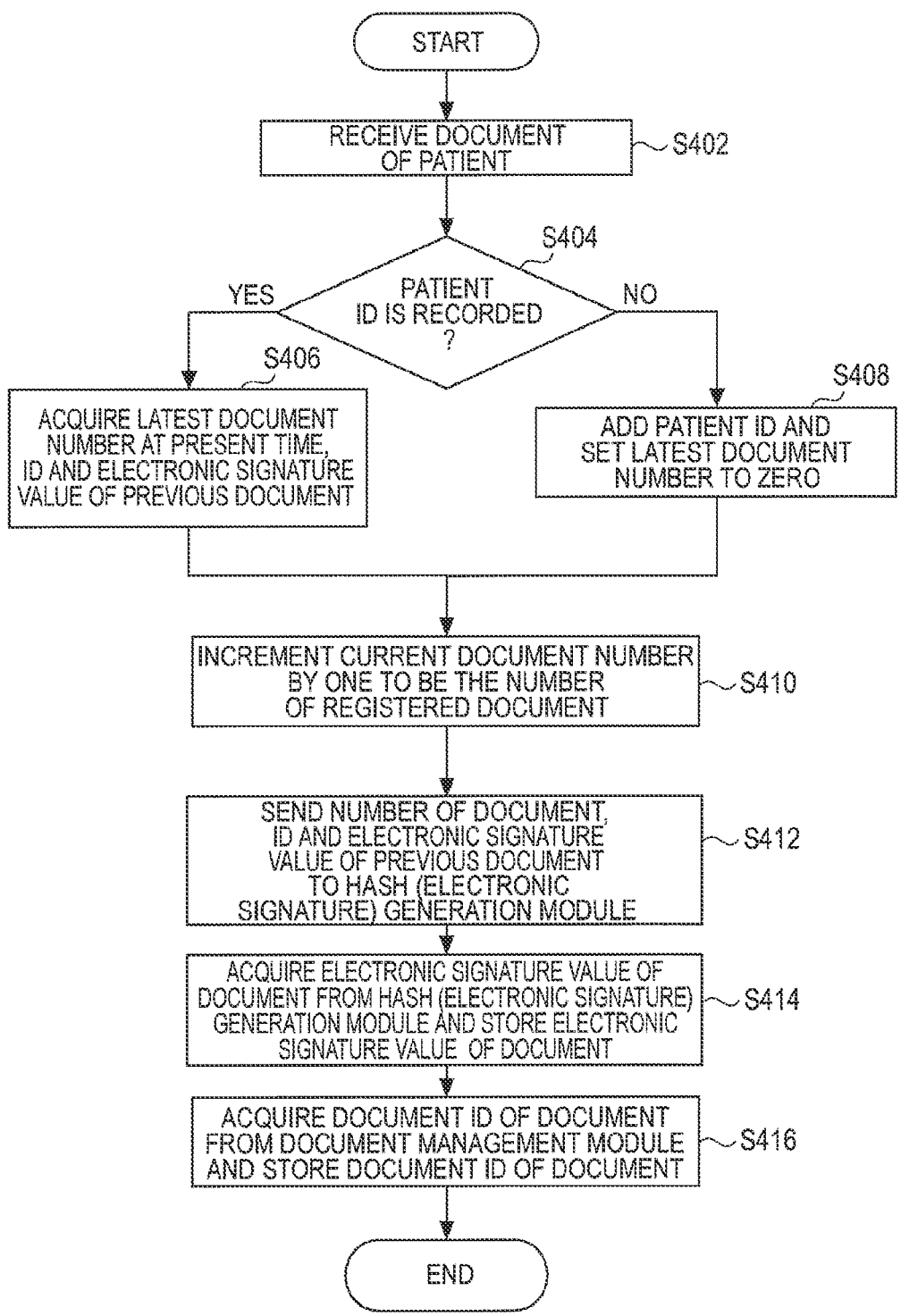
FIG. 4 is a flowchart showing an example of allocation processing by an allocation management module of this exemplary embodiment.

FIG. 4 is a flowchart showing an example of allocation processing by the allocation management module 152 of this exemplary embodiment. This is an example of allocation processing when a document with a previous document and a document with no previous document are registered.

In Step S402, a document of a patient is received from the document creation module 151.

In Step S404, it is determined whether or not the patient ID of the patient is recorded. When the patient ID is recorded, the process progresses to Step S406. Otherwise, the process progresses to Step S408.

In Step S406, the latest document number at present time, the document ID and the electronic signature value of the previous document are acquired.

In Step S408, the latest document number to which the patient ID is added is set to "0".

In Step S410, the current document number is incremented by 1, and the number of the registered document is generated.

In Step S412, the document number of the document, the document ID and the electronic signature value of the previous document are transferred to the hash (electronic signature) generation module 153.

In Step S414, the electronic signature value of the document is acquired from the hash (electronic signature) generation module 153 and stored in the document number table 600.

In Step S416, the document ID of the document is acquired from the document management module 154 and stored in the document number table 600.

Figure 7:
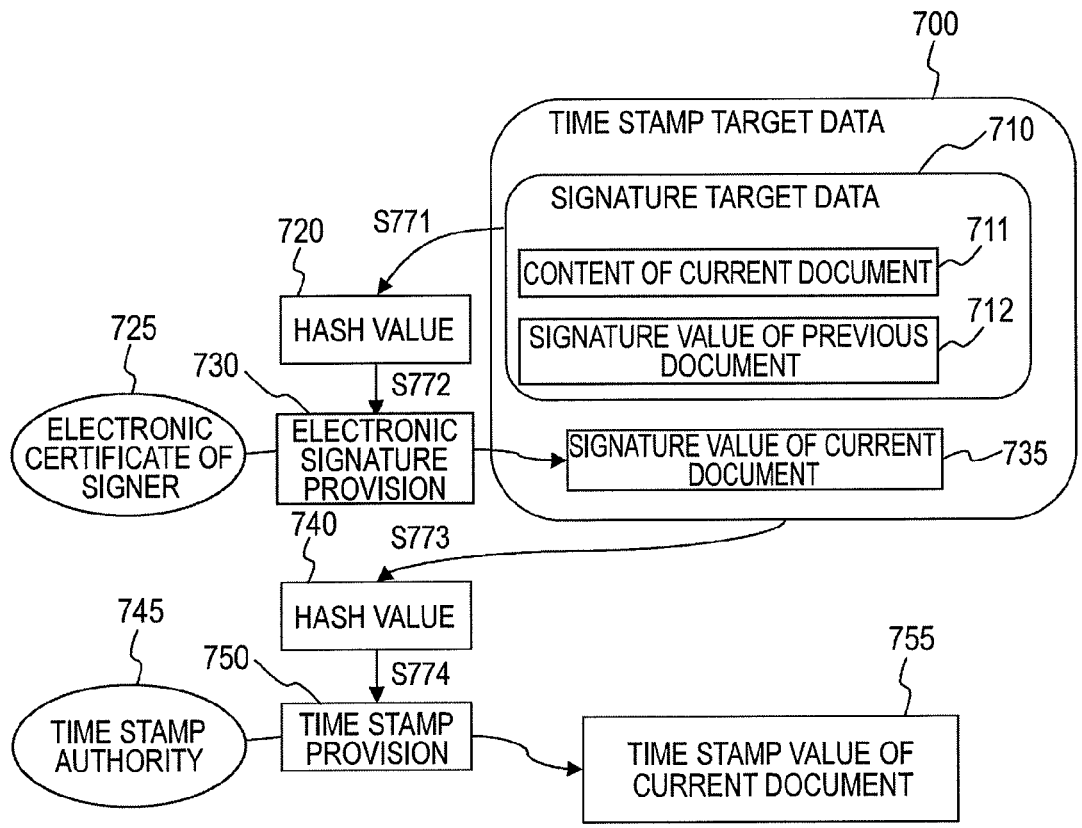
FIG. 7 is an explanatory view showing an example of a data change procedure when electronic signature and time stamp processing are performed according to this exemplary embodiment.

FIG. 7 is an explanatory view showing an example of a data change procedure when electronic signature and time stamp processing are performed according to this exemplary embodiment. Since there is no previous document, this processing is performed for the number of the current document and data of the current document.

Signature target data 710 includes the content 711 of the current document and the signature value 712 of the previous document. A hash value 720 is generated from two kinds of data of the content 711 of the current document and the signature value 712 of the previous document (Step S771). Next, electronic signature provision 730 is performed for the hash value 720 by using an electronic certificate 725 of the signer to generate the signature value 735 of the current document (Step S772).

Time stamp target data 700 includes signature target data 710 and the signature value 735 of the current document. A hash value 740 is generated from signature target data 710 and the signature value 735 of the current document (Step S773). Next, time stamp provision 750 is performed for the hash value 740 by using a time stamp authority 745 to generate a time stamp value 755 of the current document (Step S774).

Figure 5:
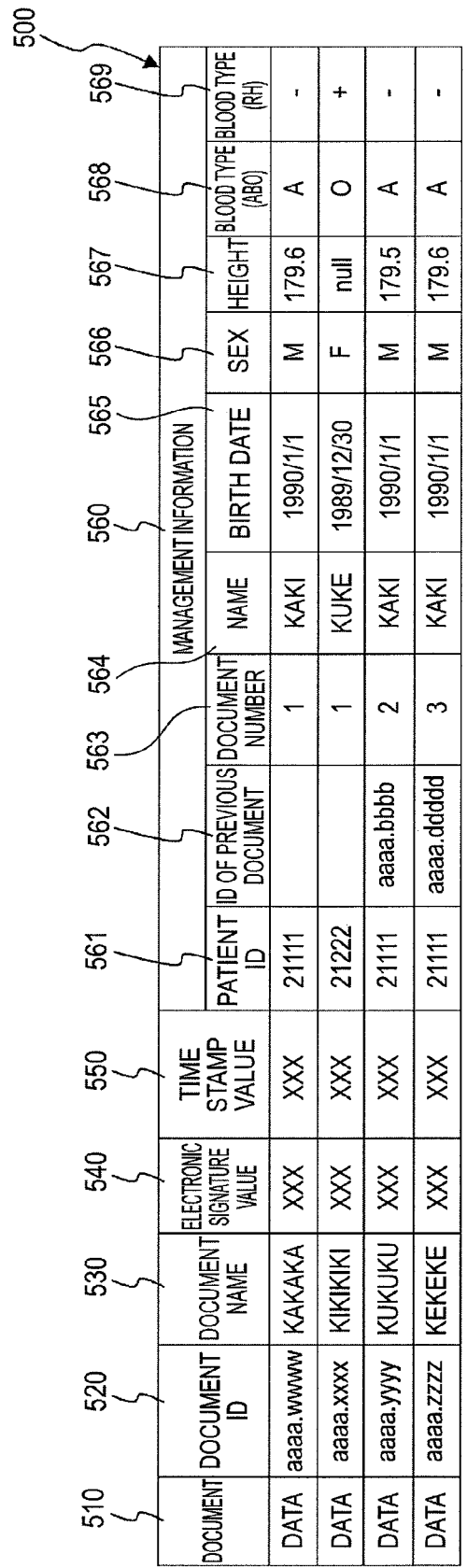
FIG. 5 is an explanatory view showing an example of the data structure of a document data table.

Data that is managed by the document management module 154 is managed in the document data table 500. FIG. 5 is an explanatory view showing an example of the data structure of the document data table 500. The document data table 500 has a document field 510, a document ID field 520, a document name field 530, an electronic signature value field 540, a time stamp value field 550, and a management information field 560.

The document field 510 stores the format (data, image, or the like) of the document.

The document ID field 520 stores the document ID for uniquely identifying the document.

The document name field 530 stores the document name of the document.

The electronic signature value field 540 stores the electronic signature value generated from the document.

The time stamp value field 550 stores the time stamp value generated from the document.

The management information field 560 has a patient ID field 561, a previous document ID field 562, a document number field 563, a name field 564, a birth date field 565, a sex field 566, a height field 567, a blood type (ABO) field 568, and a blood type (RH) field 569. Management information that is stored in the management information field 560 is acquired from the allocation management module 152, the subject data management module 110 serving as the patient system in the hospital, or the like.

(2) A document is created in a state where there is a previous document, allocation is performed, and the document is registered.

With regard to document registration of subsequent documents with the same patient ID, since there is a previous document, hash value generation and the like are performed for the signature value of the previous document (or the hash value of the document) and data of the current document. The electronic signature value and the document ID generated by the document management module 154 after document registration are sent to the allocation management module 152 and added to the document number table 600 of the allocation management module 152.

(3) The document link of the temporary patient ID is integrated to the document link of the actual patient ID.

When the actual patient ID of the patient who uses the temporary patient ID is known, integration of the document links registered with the two IDs is performed, and the document registered with the temporary patient ID is added to the document link of the actual patient ID.

FIG. 8 is a flowchart showing an example of processing for integrating a first document group and a second document group by the link management module 155 of this exemplary embodiment.

In Step S802, the patient ID and the temporary patient ID to be integrated are received.

In Step S804, it is determined whether management information of the latest document registered with the temporary patient ID is identical to management information of the latest document registered with the actual patient ID. When management information is identical, the process progresses to Step S806. Otherwise, the process progresses to Step S820.

Determination in Step S804 on whether the patients are the same person is performed by a check using the management information.

For example, determination is performed by using a same person check table 1200. FIG. 12 is an explanatory view showing an example of the data structure of the same person check table 1200. The same person check table 1200 has, in a column direction, a document field 1210, a document ID field 1220, a document name field 1230, an electronic signature value field 1240, a time stamp value field 1250, and a management information field 1260, and also has, in a row direction, an integration difference calculation result field 1282, an allowable error range field 1284, and a determination result field 1286. The management information field 1260 has a patient ID field 1261, a previous document ID field 1262, a document number field 1263, a name field 1264, a birth date field 1265, a sex field 1266, a height field 1267, a blood type (ABO) field 1268, and a blood type (RH) field 1269. There are a target for comparison A1272 with the temporary patient ID and a target for comparison B1274 with the actual patient ID.

In the example of FIG. 12, the target for comparison A1272 and the target for comparison B1274 are compared with each other in terms of the birth date field 1265, the sex field 1266, the height field 1267, the blood type (ABO) field 1268, and the blood type (RH) field 1269. A difference based on comparison is described in the integration difference calculation result field 1282. The allowable error range field 1284 stores a determination range on whether the values of the relevant fields are identical (the range in which, if the difference is within this range, it may be determined to be identical). The determination result is described in the determination result field 1286. For example, on the condition that there is no "unpermitted" in the integration difference calculation result field 1282, both documents may be integrated. Further, on the condition that the ratio of "permitted" (the ratio of "permitted" with respect to the number of fields with the allowable error range field 1284 set) is equal to or larger than a value set in advance, both documents may be integrated. The ratio of "permitted" may be calculated with the weighted values of the respective fields.

The allowable error range field 1284 in the same person check table 1200 is set in advance. The respective fields of the target for comparison A1272 and the target for comparison B1274 describe the values extracted on the basis of the temporary patient ID and the actual patient ID. Next, the difference between the fields is calculated (including comparison or the like) and is described in the integration difference calculation result field 1282. Then, determination is made on whether or not the difference is within the range of the value in the allowable error range field 1284 (including determination on whether or not the values are identical), and the determination result is described in the determination result field 1286.

As the fields for comparison, in addition to the fields shown in FIG. 12 (the birth date field 1265 and the like), determination may be made on whether the name fields 1264 are identical or not, or data for biometric authentication, such as fingerprint or the like, may be included.

In Step S806, the latest document number of the actual patient ID at present time, the document ID of the previous document, and the electronic signature value are acquired.

In Step S808, the latest document number of the temporary patient ID at present time, the document ID of the previous document, and the electronic signature value are acquired.

In Step S810, the "integration operation report" is created, and the document number is acquired from the document link of the actual patient ID. That is, the number obtained by incrementing the document number of the document of the actual patient ID by one is set as the document number of the "integration operation report".

In Step S812, the previous documents of the actual patient ID and the temporary patient ID are used, and electronic signature is provided.

In Step S814, a time stamp is provided to signed data.

In Step S816, the "integration operation report" is stored in the document management module 154.

In Step S818, the items "patient ID" and "birth date" in the management information of the document registered with the temporary patient ID are corrected.

In Step S820, a message indicating that it is not possible to confirm whether or not the patients are the same person is displayed.

Figure 11:
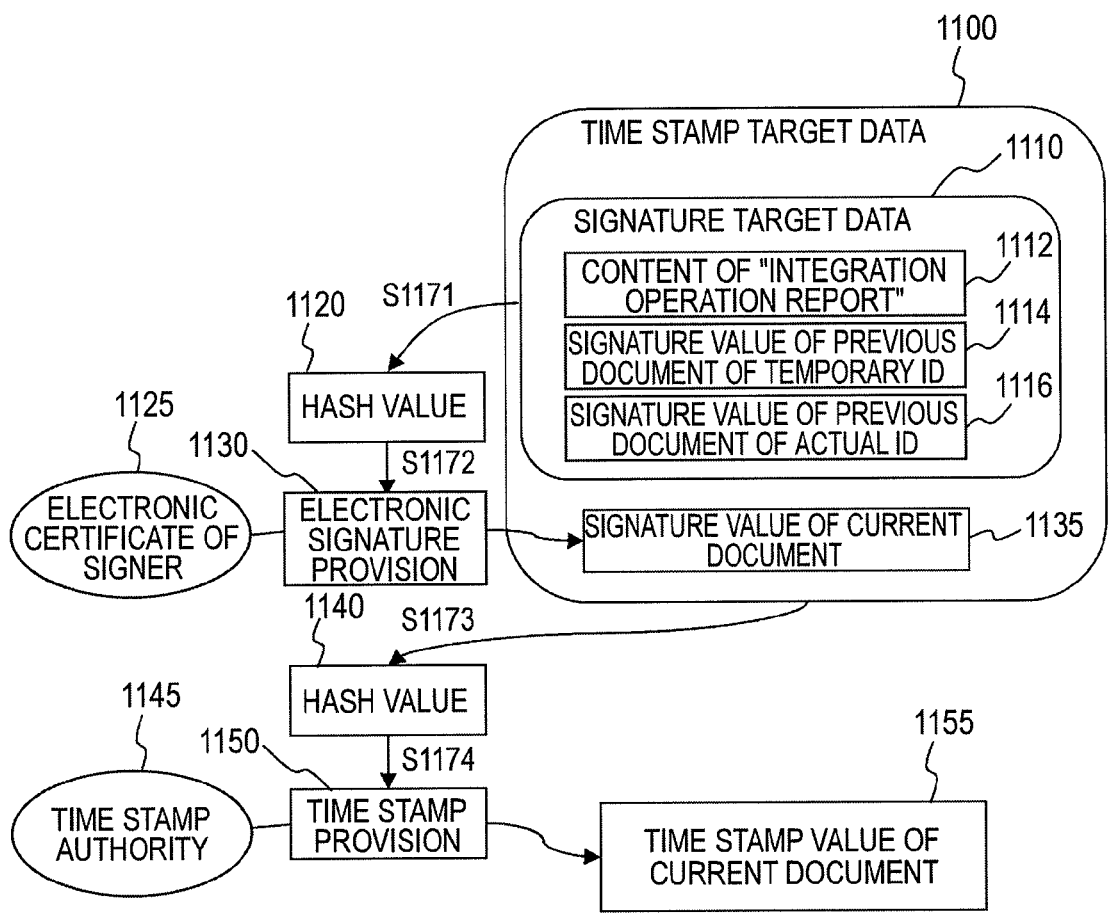
FIG. 11 is an explanatory view showing an example of a data change procedure when electronic signature and time stamp processing are performed at the time of integration processing according to this exemplary embodiment.

FIG. 11 is an explanatory view showing an example of a data change procedure when electronic signature and time stamp processing are performed at the time of integration processing according to this exemplary embodiment.

Signature target data 1110 includes the content 1112 of the "integration operation report", the signature value 1114 of the previous document of the temporary patient ID, and the signature value 1116 of the previous document of the actual patient ID. A hash value 1120 is generated from three kinds of data of the content 1112 of the "integration operation report", the signature value 1114 of the previous document of the temporary patient ID, and the signature value 1116 of the previous document of the actual patient ID (Step S1171). Next, electronic signature provision 1130 is performed for the hash value 1120 by using an electronic certificate 1125 of the signer to generate the signature value 1135 of the current document (Step S1172).

Time stamp target data 1100 includes signature target data 1110 and the signature value 1135 of the current document. A hash value 1140 is generated from signature target data 1110 and the signature value 1135 of the current document (Step S1173). Next, time stamp provision 1150 is performed for the hash value 1140 by using a time stamp authority 1145 to generate the time stamp value 1155 of the current document (Step S1174).

Figure 10:
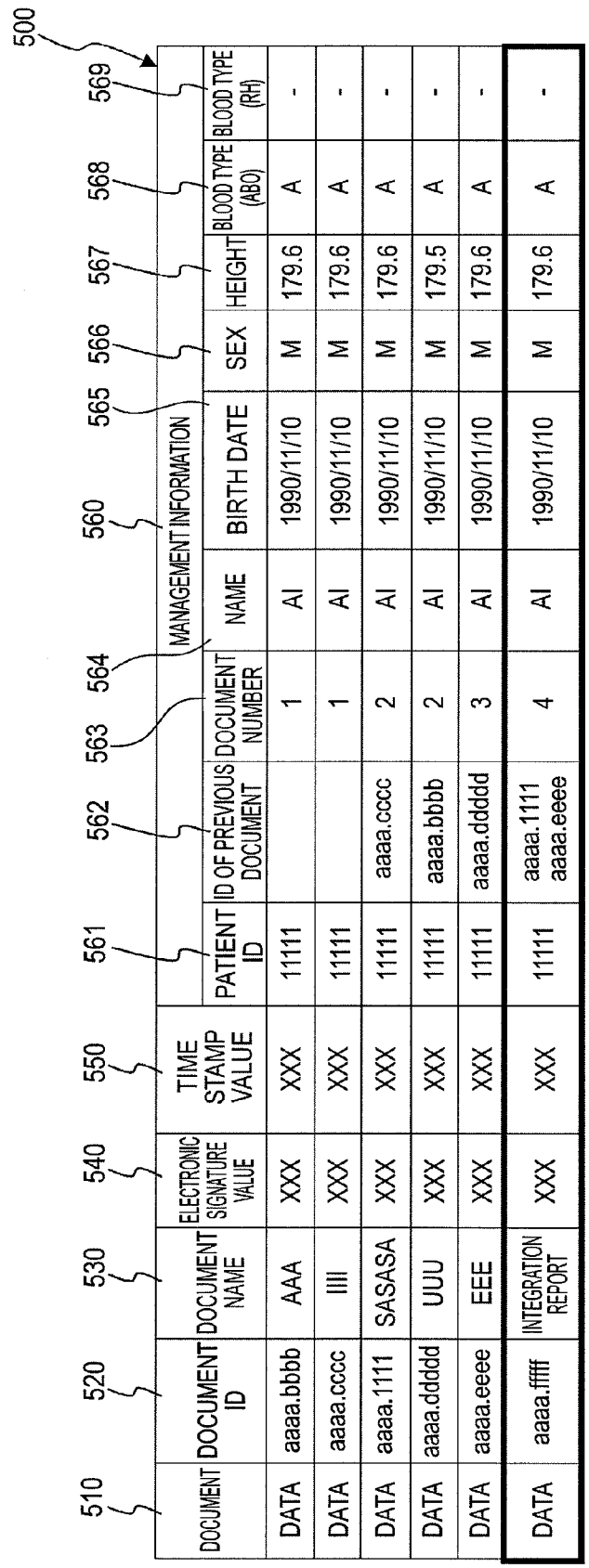
FIG. 10 is an explanatory view showing an example of the data structure of a document data table after integration processing according to this exemplary embodiment.

FIGS. 9 and 10 show examples of data changes of the document management module 154. In the document data table 500 shown in FIG. 9, "11111" as the patient ID and "temporary 123" as the temporary patient ID are stored. That is, two document groups are stored. Here, since it is known that the patient ID "11111" and the temporary patient ID "temporary 123" indicate the same person, an integration report is created and added to the last row of the document data table 500. The document number field 563 of the integration report has a value next to the document number 4 of the patient ID "11111", and the document IDs of the two documents are stored in the previous document ID field 562. With regard to the name field 564, the birth date field 565, and the like, the relevant fields of the patient ID "11111" are used. The name field 564 and the birth date field 565 of the temporary patient ID "temporary 123" are corrected to conform to the fields of the patient ID "11111". In the management data, some fields are changed before and after integration, but the content of the document is not changed. Therefore, the validity of signature and time stamp is maintained.

(4) Completeness of the Documents is Verified.

Link verification is performed in the following steps.

1. Detection of Falsification of Individual Document

Falsification entity data of the document A and electronic signature data of the previous document stored in the document management module 154 can be verified by the electronic signature and time stamp of the document A. This is the function inherent in the electronic signature and time stamp.

2. Detection of Extraction of Document Link

With the verification of the individual document, when the hash value of the (N−1)th document used for verification of the N-th document is identical to the hash value generated from the entity of the (N−1)th document, it is verified that the (N−1)th document is the previous document of the N-th document.

Figure 13:
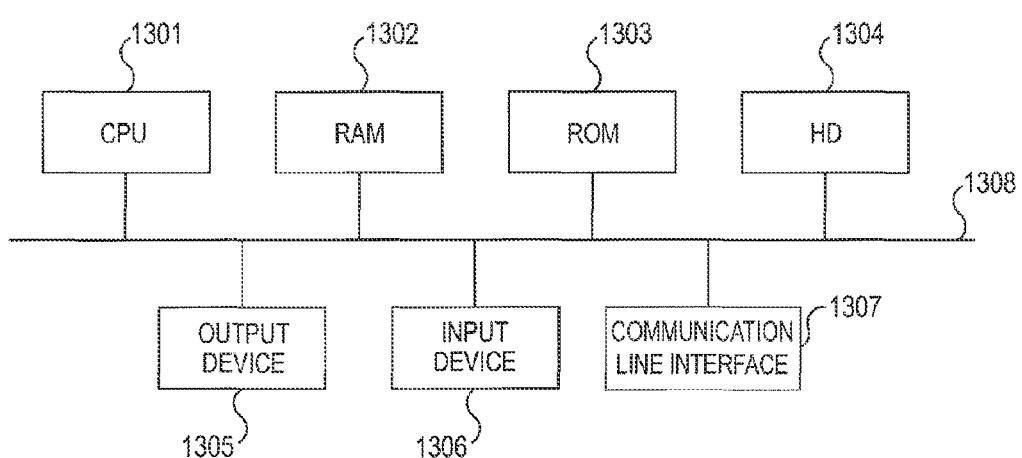
FIG. 13 is a block diagram showing an example of the hardware configuration of a computer for realizing this exemplary embodiment.

The hardware configuration of a computer on which a program as an embodiment is executed is a general computer as shown in FIG. 13, and specifically a computer that may be a personal computer or a server. That is, in a specific example, a CPU 1301 is used as a processing unit (arithmetic unit), and a RAM 1302, a ROM 1303, and an HD 1304 are used as a storage device. As the HD 1304, for example, a hard disk may be used. The computer includes the CPU 1301 that executes programs, such as the document creation module 151, the allocation management module 152, the hash (electronic signature) generation module 153, the document management module 154, the link management module 155, and the like, the RAM 1302 that stores the programs or data, the ROM 1303 that stores a program for activating this computer or the like, the HD 1304 as an auxiliary storage device, an input device 1306, such as a keyboard, a mouse, or the like, for inputting data, an output device 1305, such as a CRT or a liquid crystal display, a communication line interface 1307 for connection to a communication network, such as a network interface card or the like, and a bus 1308 for connecting the devices together to transmit and receive data. Plural computers may be connected together by a network.

In the exemplary embodiment related to the computer program of the above-described embodiments, the computer program as software is allowed to be read by a system of this hardware structure so that the software cooperates with hardware resources to realize the above-described embodiment.

The hardware configuration shown in FIG. 13 shows one configuration example. This exemplary embodiment is not limited to the configuration shown in FIG. 13, a configuration may be used which can execute the modules described in this exemplary embodiment. For example, a part of the modules may be formed with exclusive hardware (for example, ASIC or the like). A part of the modules may be provided in an external system and connected by a communication line. Plural systems shown in FIG. 13 may be connected together by the communication line and mutually cooperate. The system shown in FIG. 13 may be incorporated in an information appliance, a copy machine, a facsimile machine, a scanner, a printer, a multi-function machine (an image processing apparatus having two or more functions of the scanner, the printer, the copy machine, the facsimile machine, and the like) as well as the personal computer.

Although in the above-described embodiment, a document regarding a patient has been described, the target of the document may be other people or materials, not a patient.

The data structure described in the above-described embodiment is not limited to the data structures as described above, but other data structures may be used. For example, data having the table structure may have a link structure or the like. The data items are not limited to those shown in the drawings but may include other data items.

The above-described programs may be stored in a recording medium or may be provided through a communication means. In this case, for example, the above-described programs may be considered as inventions of "computer readable recording medium having programs recorded thereon".

"Computer readable recording medium having programs recorded thereon" refers to a recording medium that has programs recorded thereon and can be read by a computer, which is used for program installation, execution, distribution and so on.

The recording medium includes, for example, "DVD-R, DVD-RW, DVD-RAM, and the like" which are digital versatile disk (DVD) and have standards prescribed by DVD Forum, "DVD+R, DVD+RW, and the like" which have standards prescribed by DVD+RW, compact disks (CD), such as read only compact disk (CD-ROM), CD-Recordable (CD-R), CD-ReWritable (CD-RW), etc., Blu-ray Disk (registered trademark) magneto-optical disks (MO), flexible disks (FD), magnetic tapes, hard disks, read only memories (ROM), electrically erasable and programmable read only memories (EEPROM), flash memories, random access memories (RAM), or the like.

The above-described programs or some thereof may be recorded on the recording medium for conservation or distribution. Further, the above-described programs or some thereof may be transmitted by means of communication, for example, using transmission media such as wired networks used in local area network (LAN), metropolitan area network (MAN), wide area network (WAN), Internet, intranet, extranet and so on, or wireless communication networks, or combinations thereof, or may be carried on a carrier.

The programs may be a portion of a different program or may be recorded on the recording medium along with different programs or may be dividedly recorded on plural recording media. Further, the programs may be recorded in any forms such as compression and coding as long as they can be restored.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The exemplary embodiments were chosen and described in order to best explain for the skilled in the art to understand the invention for various embodiments and with the various modifications as are suited to the particular use contemplated. It is intended that the scope of the invention be defined by the following claims and their equivalents.

What is claimed is:

1. A non-transitory computer readable medium storing a program causing a computer to execute a process for information processing, the process comprising:
   receiving a first characteristic value calculated on the basis of first document information for use in detecting whether tampering with the first document information has occurred;
   receiving a second characteristic value calculated on the basis of second document information for use in detecting whether tampering with the second document information has occurred;
   calculating a third characteristic value for use in detecting whether tampering with third document information has occurred on the basis of the first characteristic value, the second characteristic value and the third document information related to integration of the first document information and the second document information; and
   generating the third document information, indicating integration of the first document information and the second document information when an instruction to integrate the first document information and the second document information is received,
   wherein the third document information is generated to include first user information for identifying a first user that initiated the integration of the first document information and the second document information, and
   wherein the third document information comprises:
      an execution request document created in response to the first user initiating the integration of the first document information and the second document information; and
      an execution confirmation document created in response to a second user confirming the integration of the first document information and the second document information initiated by the first user.

2. The non-transitory computer readable medium according to claim 1,
   wherein the third document information is generated to include an indication that a subject of the second document information is a subject of the first document information.

3. The non-transitory computer readable medium according to claim 1, the process further comprising:
   determining whether a subject of the first document information is identical to a subject of the second document information on the basis of a determination criterion set in advance,
   wherein, when the subject of the first document information and the subject of the second document information are determined to be identical, the first document information and the second document information are integrated.

4. The non-transitory computer readable medium according to claim 3,
   wherein the first document information and second document information are related to a patient in a medical field, and
   wherein the determining whether the patient as the subject of the first document information is identical to a patient as the subject of the second document information is conducted by using at least one of a name, birth date, physical information, information for biometric identification of the patient as the determination criterion set in advance.

5. The non-transitory computer readable medium of claim 1, wherein the process further comprises changing a first patient ID associated with the first document information to a second patient ID associated with the second document information upon generating the third document information.

6. An information processing apparatus comprising:
a computer processor configured to:
receive a first characteristic value calculated on the basis of first document information for use in detecting whether tampering with the first document information has occurred;
receive a second characteristic value calculated on the basis of second document information for use in detecting whether tampering with the second document information has occurred;
calculate a third characteristic value for use in detecting whether tampering with third document information has occurred on the basis of the first characteristic value, the second characteristic value and the third document information related to integration of the first document information and the second document information; and
generate the third document information which includes a message indicating integration of the first document information and the second document information when an instruction to integrate the first document information and the second document information is received,
wherein the third document information is generated to include first user information for identifying a first user that initiated the integration of the first document information and the second document information, and
wherein the third document information comprises:
an execution request document created in response to the first user initiating integration of the first document information and the second document information; and
an execution confirmation document created in response to a second user confirming the integration of the first document information and the second document information initiated by the first user.

7. An information processing method comprising:
receiving, at a processor, a first characteristic value calculated on the basis of first document information for use in detecting whether tampering with the first document information has occurred;
receiving a second characteristic value calculated on the basis of second document information for use in detecting whether tampering with the second document information has occurred;
calculating a third characteristic value for use in detecting whether tampering with third document information has occurred on the basis of the first characteristic value, the second characteristic value and the third document information related to integration of the first document information and the second document information; and
generating the third document information which includes a message indicating integration of the first document information and the second document information when an instruction to integrate the first document information and the second document information is received,
wherein the third document information is generated to include first user information for identifying a first user that initiated the integration of the first document information and the second document information, and
wherein the third document information comprises:
an execution request document created in response to the first user initiating the integration of the first document information and the second document information; and
an execution confirmation document created in response to a second user confirming the integration of the first document information and the second document information initiated by the first user.

8. A non-transitory computer readable medium storing a program causing a computer to execute a process for information processing, the process comprising:
receiving a first characteristic value calculated on the basis of first document information for use in detecting whether tampering with the first document information has occurred;
receiving a second characteristic value calculated on the basis of second document information for use in detecting whether tampering with the second document information has occurred;
generating, when it upon determining that a subject of the first document information is identical to a subject of the second document information on the basis of a determination criterion set in advance, third document information which comprises an execution request document indicating integration of the first document information and the second document information;
generating, upon determining that the subject of the first document information is not identical to the subject of the second document information on the basis of the determination criterion set in advance and upon receipt of an instruction from a first user to integrate the first document information and the second document information, the third document information comprising:
the execution request document indicating integration of the first document information and the second document information;
a first user information for identifying the first user that initiated the integration of the first document information and the second document information; and
an execution confirmation document created in response to a second user confirming the integration of the first document information and the second document information initiated by the first user; and
calculating a third characteristic value for use in detecting whether tampering with the third document information has occurred on the basis of the first characteristic value, the second characteristic value, and the third document information.

* * * * *